(12) United States Patent
Hlavinka et al.

(10) Patent No.: US 9,044,523 B2
(45) Date of Patent: *Jun. 2, 2015

(54) REDUCTION OF CONTAMINANTS IN BLOOD AND BLOOD PRODUCTS USING PHOTOSENSITIZERS AND PEAK WAVELENGTHS OF LIGHT

(75) Inventors: Dennis J. Hlavinka, Arvada, CO (US); Raymond P. Goodrich, Lakewood, CO (US); Heather Reddy, Denver, CO (US)

(73) Assignee: TERUMO BCT, INC., Lakewood, CO (US)

(*) Notice: Subject to any disclaimer, the term of this patent is extended or adjusted under 35 U.S.C. 154(b) by 1771 days.

This patent is subject to a terminal disclaimer.

(21) Appl. No.: 11/840,759

(22) Filed: Aug. 17, 2007

(65) Prior Publication Data

US 2008/0176208 A1 Jul. 24, 2008

Related U.S. Application Data

(63) Continuation-in-part of application No. 10/904,361, filed on Nov. 5, 2004, now abandoned, which is a continuation of application No. 10/357,599, filed on Feb. 3, 2002, now Pat. No. 6,843,961, which is a continuation-in-part of application No. 09/962,029, filed on Sep. 25, 2001, now abandoned, which is a continuation-in-part of application No. 09/596,429, filed on Jun. 15, 2000, now Pat. No. 7,094,378.

(60) Provisional application No. 60/822,726, filed on Aug. 17, 2006.

(51) Int. Cl.
| | |
|---|---|
| A01N 1/02 | (2006.01) |
| A61L 2/24 | (2006.01) |
| A61K 41/00 | (2006.01) |
| A61L 2/00 | (2006.01) |
| A61L 2/08 | (2006.01) |
| A61L 2/10 | (2006.01) |
| C07F 11/00 | (2006.01) |
| C07F 13/00 | (2006.01) |
| C07F 15/02 | (2006.01) |
| C07F 17/00 | (2006.01) |

(52) U.S. Cl.
CPC ............... *A61L 2/24* (2013.01); *A61K 41/0019* (2013.01); *A61L 2/0011* (2013.01); *A61L 2/0088* (2013.01); *A61L 2/08* (2013.01); *A61L 2/10* (2013.01); *C07F 11/005* (2013.01); *C07F 13/005* (2013.01); *C07F 15/02* (2013.01); *C07F 17/00* (2013.01)

(58) Field of Classification Search
CPC A61K 41/0019; A61L 2/0011; A61L 2/0088; A61L 2/08; A61L 2/10
USPC ....................... 435/2, 173.1, 173.3
See application file for complete search history.

(56) References Cited

U.S. PATENT DOCUMENTS

| | | |
|---|---|---|
| 683,690 A | 10/1901 | Johnson |
| 1,733,239 A | 10/1929 | Roberts |
| 1,961,700 A | 6/1934 | Moehler |
| 2,056,614 A | 10/1936 | Moehler |
| 2,111,491 A | 3/1938 | Kuhn et al. |
| 2,212,230 A | 8/1940 | Goldmann |
| 2,212,330 A | 8/1940 | Thomas |
| 2,340,890 A | 2/1944 | Lang et al. |
| 2,654,735 A | 10/1953 | Funk et al. |
| 2,825,729 A | 3/1958 | Petering et al. |
| 3,189,598 A | 6/1965 | Yagi et al. |
| 3,456,053 A | 7/1969 | Crawford |
| 3,683,177 A | 8/1972 | Veloz |
| 3,683,183 A | 8/1972 | Vizzini et al. |
| 3,705,985 A | 12/1972 | Manning et al. |
| 3,776,694 A | 12/1973 | Leittl |
| 3,852,032 A | 12/1974 | Urbach |
| 3,864,081 A | 2/1975 | Logrippo |
| 3,894,236 A | 7/1975 | Hazelrigg |
| 3,920,650 A | 11/1975 | Spencer et al. |
| 3,926,556 A | 12/1975 | Boucher |
| 3,927,325 A | 12/1975 | Hungate et al. |
| 4,124,598 A | 11/1978 | Hearst et al. |
| 4,139,348 A | 2/1979 | Swartz |
| 4,167,669 A | 9/1979 | Panico |
| 4,169,204 A | 9/1979 | Hearst et al. |
| 4,173,631 A | 11/1979 | Graham et al. |

(Continued)

FOREIGN PATENT DOCUMENTS

| | | |
|---|---|---|
| DE | 3930510 | 3/1991 |
| DE | 4235841 | 4/1994 |

(Continued)

OTHER PUBLICATIONS http://www.buzzle.com/articles/wavelength-of-visible-light-spectrum.html wesite for the wavelngths for visible light downloaded Dec. 10, 2010.*
Tsugita et al. Biochim. biophys. Acta (1965) 103: 360-363.*
Kuratomi et al. FEBS Lett. (1976) 72(2): 295-298, full paper.*
STN Registry File for riboflavin downloaded Dec. 6, 2010.*
Matsuki et al. Rinsho Kagaku Shinojuma (1978; Volume date 1977) 17: 191-2 (abstract only).*
Webpage from the PhyLink.com website http://www.physlink.com/Education/AskExperts/ae300.cfm downloaded Sep. 28, 2014.*

(Continued)

*Primary Examiner* — Susan Hanley
(74) *Attorney, Agent, or Firm* — René A. Pereyra; Elizabeth J. Reagan; John R. Merkling (57) ABSTRACT

Methods and apparatuses are provided for reduction of pathogens in fluids containing blood products. Preferred methods include the steps of adding an effective, non-toxic amount of a photosensitizer such as riboflavin to the blood product and exposing the fluid to light having a peak wavelength.

6 Claims, 8 Drawing Sheets

(56) References Cited

U.S. PATENT DOCUMENTS

| | | |
|---|---|---|
| 4,181,128 A | 1/1980 | Swartz |
| 4,196,281 A | 4/1980 | Hearst et al. |
| 4,312,883 A | 1/1982 | Baccichetti et al. |
| 4,321,918 A | 3/1982 | Clark, II |
| 4,321,919 A | 3/1982 | Edelson |
| 4,336,809 A | 6/1982 | Clark |
| 4,398,031 A | 8/1983 | Bender et al. |
| 4,398,906 A | 8/1983 | Edelson |
| 4,402,318 A | 9/1983 | Swartz |
| 4,407,282 A | 10/1983 | Swartz |
| 4,421,987 A | 12/1983 | Herold |
| 4,424,201 A | 1/1984 | Valinsky et al. |
| 4,428,744 A | 1/1984 | Edelson |
| 4,447,415 A | 5/1984 | Rock et al. |
| 4,456,512 A | 6/1984 | Bieler et al. |
| 4,464,166 A | 8/1984 | Edelson |
| 4,464,336 A | 8/1984 | Hiramoto |
| 4,467,206 A | 8/1984 | Taylor et al. |
| 4,481,167 A | 11/1984 | Ginter et al. |
| 4,493,981 A | 1/1985 | Payne |
| 4,568,328 A | 2/1986 | King |
| 4,573,960 A | 3/1986 | Goss |
| 4,573,961 A | 3/1986 | King |
| 4,573,962 A | 3/1986 | Troutner |
| 4,576,143 A | 3/1986 | Clark, III |
| 4,578,056 A | 3/1986 | King et al. |
| 4,596,547 A | 6/1986 | Troutner |
| 4,604,356 A | 8/1986 | Blake, II |
| 4,608,255 A | 8/1986 | Kahn et al. |
| 4,612,007 A | 9/1986 | Edelson |
| 4,613,322 A | 9/1986 | Edelson |
| 4,614,190 A | 9/1986 | Stanco et al. |
| 4,623,328 A | 11/1986 | Hartranft |
| 4,642,171 A | 2/1987 | Sekine et al. |
| 4,645,649 A | 2/1987 | Nagao |
| 4,648,992 A | 3/1987 | Graf et al. |
| 4,649,151 A | 3/1987 | Dougherty et al. |
| 4,651,739 A | 3/1987 | Oseroff et al. |
| 4,683,195 A | 7/1987 | Mullis et al. |
| 4,683,202 A | 7/1987 | Mullis |
| 4,683,889 A | 8/1987 | Edelson |
| 4,684,521 A | 8/1987 | Edelson |
| 4,693,981 A | 9/1987 | Wiesehahn et al. |
| 4,695,460 A | 9/1987 | Holme |
| 4,708,715 A | 11/1987 | Troutner et al. |
| 4,726,949 A | 2/1988 | Miripol et al. |
| 4,727,027 A | 2/1988 | Wiesehahn et al. |
| 4,737,140 A | 4/1988 | Lee et al. |
| 4,748,120 A | 5/1988 | Wiesehahn |
| 4,775,625 A | 10/1988 | Sieber |
| 4,788,038 A | 11/1988 | Matsunaga |
| RE32,874 E | 2/1989 | Rock et al. |
| 4,831,268 A | 5/1989 | Fisch et al. |
| 4,833,165 A | 5/1989 | Louderback |
| 4,861,704 A | 8/1989 | Reemtsma et al. |
| 4,866,282 A | 9/1989 | Miripol et al. |
| 4,871,559 A | 10/1989 | Dunn et al. |
| 4,878,891 A | 11/1989 | Judy et al. |
| 4,880,512 A | 11/1989 | Cornelius et al. |
| 4,880,788 A | 11/1989 | Moake et al. |
| 4,910,942 A | 3/1990 | Dunn et al. |
| 4,915,683 A | 4/1990 | Sieber |
| 4,921,473 A | 5/1990 | Lee et al. |
| 4,930,516 A | 6/1990 | Alfano et al. |
| 4,946,438 A | 8/1990 | Reemtsma et al. |
| 4,948,980 A | 8/1990 | Wedekamp |
| 4,950,665 A | 8/1990 | Floyd |
| 4,952,812 A | 8/1990 | Miripol et al. |
| 4,960,408 A | 10/1990 | Klainer et al. |
| 4,961,928 A | 10/1990 | Holme et al. |
| 4,978,688 A | 12/1990 | Louderback |
| 4,986,628 A | 1/1991 | Lozhenko et al. |
| 4,992,363 A | 2/1991 | Murphy |
| 4,994,367 A | 2/1991 | Bode et al. |
| 4,998,931 A | 3/1991 | Slichter et al. |
| 4,999,375 A | 3/1991 | Bachynsky et al. |
| 5,011,695 A | 4/1991 | Dichtelmuller et al. |
| 5,017,338 A | 5/1991 | Surgenor |
| 5,020,995 A | 6/1991 | Levy |
| 5,030,200 A | 7/1991 | Judy et al. |
| 5,034,235 A | 7/1991 | Dunn et al. |
| 5,039,483 A | 8/1991 | Sieber et al. |
| 5,041,078 A | 8/1991 | Matthews et al. |
| 5,089,146 A | 2/1992 | Carmen et al. |
| 5,089,384 A | 2/1992 | Hale |
| 5,092,773 A | 3/1992 | Levy |
| 5,095,115 A | 3/1992 | Grimmer et al. |
| 5,114,670 A | 5/1992 | Duffey |
| 5,114,957 A | 5/1992 | Hendler et al. |
| 5,120,649 A | 6/1992 | Horowitz et al. |
| 5,123,902 A | 6/1992 | Müller et al. |
| 5,133,932 A | 7/1992 | Gunn et al. |
| 5,147,776 A | 9/1992 | Koerner, Jr. |
| 5,150,705 A | 9/1992 | Stinson |
| 5,166,528 A | 11/1992 | Le Vay |
| 5,184,020 A | 2/1993 | Hearst et al. |
| 5,185,532 A | 2/1993 | Zabsky et al. |
| 5,192,264 A | 3/1993 | Fossel |
| 5,216,251 A | 6/1993 | Matschke |
| 5,229,081 A | 7/1993 | Suda |
| 5,232,844 A | 8/1993 | Horowitz et al. |
| 5,234,808 A | 8/1993 | Murphy |
| 5,235,045 A | 8/1993 | Lewis et al. |
| 5,236,716 A | 8/1993 | Carmen et al. |
| 5,247,178 A | 9/1993 | Ury et al. |
| 5,248,506 A | 9/1993 | Holme et al. |
| 5,258,124 A | 11/1993 | Bolton et al. |
| 5,269,946 A | 12/1993 | Goldhaber et al. |
| 5,273,713 A | 12/1993 | Levy |
| 5,288,605 A | 2/1994 | Lin et al. |
| 5,288,647 A | 2/1994 | Zimlich, Jr. et al. |
| 5,290,221 A | 3/1994 | Wolf, Jr. et al. |
| 5,300,019 A | 4/1994 | Bischof et al. |
| 5,304,113 A | 4/1994 | Sieber et al. |
| 5,318,023 A | 6/1994 | Vari et al. |
| 5,340,716 A | 8/1994 | Ullman et al. |
| 5,342,752 A | 8/1994 | Platz et al. |
| 5,344,752 A | 9/1994 | Murphy |
| 5,344,918 A | 9/1994 | Dazey et al. |
| 5,358,844 A | 10/1994 | Stossel et al. |
| 5,360,734 A | 11/1994 | Chapman et al. |
| 5,366,440 A | 11/1994 | Fossel |
| 5,376,524 A | 12/1994 | Murphy et al. |
| 5,378,601 A | 1/1995 | Gepner-Puszkin |
| 5,418,130 A | 5/1995 | Platz et al. |
| 5,419,759 A | 5/1995 | Naficyn |
| 5,427,695 A | 6/1995 | Brown |
| 5,427,920 A | 6/1995 | Berndt et al. |
| 5,433,738 A | 7/1995 | Stinson |
| 5,459,030 A | 10/1995 | Lin et al. |
| 5,466,573 A | 11/1995 | Murphy et al. |
| 5,474,891 A | 12/1995 | Murphy |
| 5,482,828 A | 1/1996 | Lin et al. |
| 5,484,778 A | 1/1996 | Kenney et al. |
| 5,487,971 A | 1/1996 | Holme et al. |
| 5,489,442 A | 2/1996 | Dunn et al. |
| 5,503,721 A | 4/1996 | Hearst et al. |
| 5,516,629 A | 5/1996 | Park et al. |
| 5,527,704 A | 6/1996 | Wolf, Jr. et al. |
| 5,536,238 A | 7/1996 | Bischof |
| 5,545,516 A | 8/1996 | Wagner |
| 5,547,635 A | 8/1996 | Duthie et al. |
| 5,550,111 A | 8/1996 | Suhadolnik et al. |
| 5,556,958 A | 9/1996 | Carroll et al. |
| 5,556,993 A | 9/1996 | Wollowitz et al. |
| 5,557,098 A | 9/1996 | D'Silva |
| 5,569,579 A | 10/1996 | Murphy |
| 5,571,666 A | 11/1996 | Floyd et al. |
| 5,587,490 A | 12/1996 | Goodrich, Jr. et al. |
| 5,593,823 A | 1/1997 | Wollowitz et al. |
| 5,597,722 A | 1/1997 | Chapman et al. |
| 5,607,924 A | 3/1997 | Magda et al. |
| 5,622,867 A | 4/1997 | Livesey et al. |
| 5,624,435 A | 4/1997 | Furumoto et al. |

(56) References Cited

U.S. PATENT DOCUMENTS

| | | | |
|---|---|---|---|
| 5,628,727 A | 5/1997 | Hakky et al. | |
| 5,639,376 A | 6/1997 | Lee et al. | |
| 5,639,382 A | 6/1997 | Brown | |
| 5,643,334 A | 7/1997 | Eckhouse et al. | |
| 5,652,096 A | 7/1997 | Cimino | |
| 5,653,887 A | 8/1997 | Wahl et al. | |
| 5,654,443 A | 8/1997 | Wollowitz et al. | |
| 5,658,530 A | 8/1997 | Dunn | |
| 5,658,722 A | 8/1997 | Margolis-Nunno et al. | |
| 5,683,661 A | 11/1997 | Hearst et al. | |
| 5,683,768 A | 11/1997 | Shang et al. | |
| 5,686,436 A | 11/1997 | Van Dyke | |
| 5,688,475 A | 11/1997 | Duthie, Jr. | |
| 5,691,132 A | 11/1997 | Wollowitz et al. | |
| 5,698,524 A | 12/1997 | Mach et al. | |
| 5,698,677 A | 12/1997 | Eibl et al. | |
| 5,698,866 A | 12/1997 | Doiron et al. | |
| 5,702,684 A | 12/1997 | McCoy et al. | |
| 5,707,401 A | 1/1998 | Talmore | |
| 5,709,653 A | 1/1998 | Leone | |
| 5,709,991 A | 1/1998 | Lin et al. | |
| 5,712,086 A | 1/1998 | Horowitz et al. | |
| 5,714,328 A | 2/1998 | Magda et al. | |
| 5,739,013 A | 4/1998 | Budowsky et al. | |
| 5,756,553 A | 5/1998 | Iguchi et al. | |
| 5,762,867 A | 6/1998 | D'Silva | |
| 5,768,853 A | 6/1998 | Bushnell et al. | |
| 5,772,960 A | 6/1998 | Ito et al. | |
| 5,786,598 A | 7/1998 | Clark et al. | |
| 5,789,150 A | 8/1998 | Margolis-Nunno et al. | |
| 5,789,601 A | 8/1998 | Park et al. | |
| 5,798,238 A | 8/1998 | Goodrich, Jr. et al. | |
| 5,798,523 A | 8/1998 | Villeneuve et al. | |
| 5,811,144 A | 9/1998 | Bordeleau et al. | |
| 5,817,519 A | 10/1998 | Zelmanovic et al. | |
| 5,827,644 A | 10/1998 | Floyd et al. | |
| 5,834,198 A | 11/1998 | Famulok et al. | |
| 5,843,459 A | 12/1998 | Wang et al. | |
| 5,846,961 A | 12/1998 | Van Dyke | |
| 5,854,967 A | 12/1998 | Hearst et al. | |
| 5,866,074 A | 2/1999 | Chapman et al. | |
| 5,868,695 A | 2/1999 | Wolf, Jr. et al. | |
| 5,869,701 A | 2/1999 | Park et al. | |
| 5,871,900 A | 2/1999 | Wollowitz et al. | |
| 5,876,676 A | 3/1999 | Stossel et al. | |
| 5,891,705 A | 4/1999 | Budowsky et al. | |
| 5,900,211 A | 5/1999 | Dunn et al. | |
| 5,908,742 A | 6/1999 | Lin et al. | |
| 5,922,278 A | 7/1999 | Chapman et al. | |
| 5,925,885 A | 7/1999 | Clark et al. | |
| 5,935,092 A | 8/1999 | Sun et al. | |
| 5,951,509 A | 9/1999 | Morris | |
| 5,976,884 A | 11/1999 | Chapman et al. | |
| 6,004,741 A | 12/1999 | Wollowitz et al. | |
| 6,013,918 A | 1/2000 | Bushnell et al. | |
| 6,020,333 A | 2/2000 | Berque | |
| 6,054,097 A | 4/2000 | Mass et al. | |
| 6,077,659 A * | 6/2000 | Ben-Hur et al. | 435/2 |
| 6,087,141 A | 7/2000 | Margolis-Nunno et al. | |
| 6,158,319 A | 12/2000 | D'Silva | |
| 6,165,711 A | 12/2000 | Dorner et al. | |
| 6,200,287 B1 | 3/2001 | Keller et al. | |
| 6,228,332 B1 | 5/2001 | Dunn et al. | |
| 6,258,577 B1 | 7/2001 | Goodrich et al. | |
| 6,261,518 B1 | 7/2001 | Caputo et al. | |
| 6,268,120 B1 | 7/2001 | Platz et al. | |
| 6,277,337 B1 | 8/2001 | Goodrich et al. | |
| 6,312,931 B1 | 11/2001 | O'Dwyer et al. | |
| 6,329,136 B1 | 12/2001 | Lagunas-Solar et al. | |
| 6,348,309 B1 | 2/2002 | Mohr et al. | |
| 6,379,697 B1 * | 4/2002 | Gregoriadis et al. | 424/450 |
| 6,433,343 B1 | 8/2002 | Cimino et al. | |
| 6,565,802 B1 | 5/2003 | Hanley et al. | |
| 6,586,749 B2 | 7/2003 | Cimino et al. | |
| 6,843,961 B2 | 1/2005 | Hlavinka et al. | |
| 6,855,489 B1 | 2/2005 | Herman et al. | |
| 6,949,753 B2 | 9/2005 | Cimino et al. | |
| 6,986,867 B2 | 1/2006 | Hanley et al. | |
| 7,049,110 B2 * | 5/2006 | Reddy et al. | 435/173.1 |
| 7,094,378 B1 * | 8/2006 | Goodrich et al. | 422/22 |
| 2001/0046662 A1 * | 11/2001 | Wagner et al. | 435/2 |
| 2003/0085173 A1 | 5/2003 | deGheldere et al. | |
| 2003/0146162 A1 | 8/2003 | Metzel et al. | |
| 2003/0165398 A1 | 9/2003 | Waldo et al. | |
| 2003/0215784 A1 * | 11/2003 | Dumont et al. | 435/2 |
| 2004/0072139 A1 | 4/2004 | Mohr | |
| 2004/0081956 A1 * | 4/2004 | Lockerbie et al. | 435/2 |
| 2004/0088189 A1 | 5/2004 | Veome et al. | |
| 2005/0137517 A1 | 6/2005 | Blickhan et al. | |
| 2005/0258109 A1 | 11/2005 | Hanley et al. | |
| 2007/0212379 A1 * | 9/2007 | Goodrich | 424/277.1 |

FOREIGN PATENT DOCUMENTS

| | | |
|---|---|---|
| DE | 10031851 | 1/2002 |
| EP | 0 066 886 | 8/1982 |
| EP | 0 124 363 | 4/1984 |
| EP | 0 196 515 | 10/1986 |
| EP | 0 679 398 | 11/1995 |
| EP | 0 801 072 | 10/1997 |
| EP | 0 525 138 | 9/1998 |
| FR | 2674753 | 10/1992 |
| FR | 2696319 | 4/1994 |
| FR | 2715303 | 7/1995 |
| FR | 2718353 | 10/1995 |
| GB | 2212010 | 7/1989 |
| WO | WO89/06702 | 7/1989 |
| WO | WO91/02529 | 3/1991 |
| WO | WO92/11057 | 7/1992 |
| WO | WO92/17173 | 9/1992 |
| WO | WO93/21992 | 11/1993 |
| WO | WO94/07426 | 4/1994 |
| WO | WO94/07499 | 4/1994 |
| WO | WO95/02325 | 1/1995 |
| WO | WO95/11028 | 4/1995 |
| WO | WO95/12973 | 5/1995 |
| WO | WO95/16348 | 6/1995 |
| WO | WO96/14740 | 5/1996 |
| WO | WO 9718844 A1 * | 5/1997 |
| WO | WO97/07674 | 6/1997 |
| WO | WO97/22245 | 6/1997 |
| WO | WO97/36581 | 9/1997 |
| WO | WO97/36634 | 9/1997 |
| WO | WO98/30545 | 7/1998 |
| WO | WO98/31219 | 7/1998 |
| WO | WO99/11305 | 11/1999 |
| WO | WO00/04930 | 2/2000 |
| WO | WO00/47240 | 8/2000 |
| WO | WO00/74731 | 12/2000 |
| WO | WO01/23007 | 4/2001 |
| WO | WO01/28599 | 4/2001 |
| WO | WO01/96340 | 12/2001 |
| WO | WO02/26270 | 4/2002 |

OTHER PUBLICATIONS

Abdursashidova, GG et al, "Polynucleotide-protein interactions in the translation system. Identification of proteins interacting with tRNA in the A- and P-sites of E. Coli ribosomes," 1979 *Nucleic Acids Res.* 6(12):3891-3909.

Andreu, et al, "Ultraviolet irradiation of platelet concentrates: feasibility in transfusion practice", *Transfusion*, v. 30, No. 5, 1990 pp. 401-406.

Bhatia, J. et al., "Riboflavin Enhances Photo-oxidation of Amino Acids under Simulated Clinical Conditions," *J. Parenteral Enteral Nutr.* 1983, 7(3):277-279.

Brodie et al, "Mode of Action of Vitamin K in Microorganisms," 1966, *Vitam. Horm.* 24:447-463.

Budowsky et al, "Induction of polynucleotide-protein cross-linkages by ultraviolet irradiation," 1986, *Eur. J. Biochem.* 159:95-101.

Budowsky et al, "Preparation of cyclic 2',3'-monophosphates of oligoadenylates (A2'p)nA>p and A3'p(A2'p)n-1A>p," 1994, *Eur. J. Biochem.* 220:97-104.

(56) References Cited

OTHER PUBLICATIONS

Budowsky et al, "Principles of selective inactivation of viral genome. VI, Inactivation of The infectivity of the influenza virus by the action of (β-propiolactone," 1991, *Vaccine* 9:398-402.

Budowsky et al, "Principles of selective inactivation of viral genome. VII, Some peculiarities in determination of viral suspension infectivity during inactivation by chemical agents,", 1991, *Vaccine* 9:473-476.

Budowsky et al, "Principles of selective inactivation of viral genome. VIII, The influence of (β-propiolactone on immunogenic and protective activities of influenza virus,", 1993, *Vaccine* 11(3):343-348.

Budowsky, EI, "Problems and Prospects for Preparation of Killed Antiviral Vaccines", 1991, *Adv. Virus Res.* 39:255-290.

Budowsky, et al "Polynucleotide-Protein Cross-Links Induced by Ultraviolet Light and Their Use for Structural investigation of Nucleoproteins," 1989, *Progress in Nucleic Acid Res. and Mol. Bio* 37:1-65.

Cadet, J. et al., "Mechanisms and Products of Photosensitized Degradation of Nucleic Acids and Related Model Compounds," 1983, *Israel J. Chem.* 23:420-429.

Chastain et al, "Clarification and Quantitation of Primary (Tissue) and Secondary (Microbial) Catabolites of Riboflavin That are Excreted in Mammalian (Rat) urine,"*J. Nutr.*, 1987, pp. 468-475.

Chastain et al, "Flavin Metabolites", in *Chemistry and Biochemistry of Flavoenzymes*, vol. I, Chapter 6, Muller, F. (ed.), CRC Press, Boston, 1991, pp. 195-200.

Chow et al, "Recognition of G-U mismatches by tris(47-diphenyl-110-phenanthroline)rhodium(III)," 1992 *Biochemistry* 31(24):5423-5429.

Deutsch, E. "Vitamin K in Medical Practice: Adults," 1966, *Vitam. Horm.*, 24:665-680.

Edwards et al, "Visible light effects on tumoral cells in a culture medium enriched with tryptophan and riboflavin", *J. Photochem. Photobiol. B:Biol.* 1994, 24:179-186.

Ennever et al. (1983), "Potential for Genetic Damage from Multivitamin Solutions Exposed to Phototherapy Illumination,"*Pediatr. Res.* 17:192-194.

Ennever, et al, "Short Communication Photochemical Reactions of Riboflavin: Covalent Binding to DNA and to Poly (dA)☐Poly (dT)", *Pediatr. Res.*, 1983, 17:234-236.

Everett et al, "Aryl-2-halogenoalkylamines. Part XII. Some Carboxylic Derivatives of NN-Di-2-chloroethylaniline", *J. Chem. Soc.*, 1952, pp. 2386-2392.

Friedman, et al, "Reducing the Infectivity of Blood Components—What we have learned", 1995, *Immunological Investigations* 24 1&2: 49-71.

Fritz et al, "Photochemical Properties of Flavin Derivatives", *Photochem. Photobiol.*, 1987, 45(1):113-117.

Fritz et al, "Triplet Lifetimes of Some Flavins", *Photochem. Photobiol.*, 1987, 45(4):539-541.

Galston, A.W., "Riboflavin-sensitized Photooxidation of Indole-acetic Acid and Related Compounds", *Proc. Natl. Acad. Sci.*, 1949, 35:10-17.

Ghiron et al, "The Flavin-sensitized Photoinactivation of Trypsin", *Photochemistry and Photobiology*, 1965, 4:13-26.

Golding et al, "Eradication of bacterial species via photosensitization", *SPIE*, vol. 3563, 9/98, pp. 18-27.

Goodrich et al, "The design and development of selective, photoactivated drugs for sterilization of blood products," 1997, *Drugs of the Future* 22(2):159-171.

Gordon-Walker et al, "Excited States of Flavins Characterised by Absorption, Prompt and Delayed Emission Spectra", *Eur. J. Biochem.*, 1970, 13:313-321.

Halwer, Murray, "The Photochemistry of Riboflavin and Related Compounds", *J. Am. Chem. Soc.*, 1951, 73:4870-4874.

Hanson, CV, "Photochemical Inactivation of Deoxyribonucleic and Ribonucleic Acid Viruses by Chlorpromazine", *Antimicrob. Agent Chemother.*, 1979, 15(3):461-464.

Hemmerich, V.P. "Flavosemichinon-Metallchelate: Modelle zür Erklärung der 'active site' in den mitochondrialen Flavoenzymen Zum Verhalten des Riboflavins gegen Metallionen III," *Helv. Chim. Acta,* 1964, 47(55):464-465, in German.

Herfeld et al, "Synthesis, DNA-binding properties and cytotoxic activity of flavino-ligopyrrolecarboxamide and flavin-oligoimidazolecarboxamide conjugates", *Anti-Cancer Drug Design,* 1988, 13:337-359.

Hoffmann et al, R, "DNA Strand Breaks in mammalian Cells Exposed to Light in the Presence of Riboflavin and Tryptophan," *Photochemistry and Photobiology* 1979 29:299-303.

Ito et al, "Hydroxydeoxyguanosine Formation at the 5' Site of 5'-GG-3' Sequences in Double-stranded DNA by UV Radiation with Riboflavin", *J. Biol. Chem,* 1993,. 285(18):13221-13227.

Ivanchenko, VA et al, "The photochemistry of purine components of nucleic acids. I. The efficiency of photolysis of adenine and guanine derivatives in aqueous solution", *Nucleic Acids Res,* 1974, 2(8):1365-1373.

Johnston et al, "Low-level Psoralen-deoxyribonucleic Acid Crosslinks induced by Single Laser Pulses", *Biochemistry*, 1981, 20, 739-745.

Joshi, P.C., "Comparison of the DNA-damaging property of photosensitized riboflavin via singlet oxygen (1O2) and superoxide radical (Oi) mechanisms", Toxicology Letters, 1985, 26:211-217.

Kabuta et al. (1978), "Inactivation of viruses by dyes and visible light," Chem. *Abstracts* 87(1), Abstract No. 400626.

Kale et al., "Assessment of the genotoxic potential of riboflavin and lumiflavin; B. Effect of light", *Mutation Res.*, 1992, 298:17-23.

Karrer et al., "Weitere Synthesen Lactoflavin-ähnlicher Verbindungen II," *Helv. Chim. Acta,* 1934, 16:1516-1522, in German.

Kasai et al, "Purification, Properties, and Function of Flavokinase from Rat Intestinal Mucosa," *J. Biochem.*, 1990, 107(2):298-303.

Kasai et al. "Intestinal Absorption of Riboflavin, Studied by an in Situ Circulation System Using Radioactive Analogues", *J. Nutr. Sci. Vitaminol.,* 1988, 34:265-280.

Kasai, et al, "Photosensitized Formation of 7,8-Dihydro-8-oxo-2'-deoxyguanosine (8-Hydroxy-2'-deoxyguanosine) in DNA by Riboflavin: A Non Singlet Oxygen Mediated Reaction", *J. Am. Chem. Soc.*, 1992, 114:9692-9694.

Kimmich et al, "Paper Chromatography of Flavin Analogues," *J. Chromatogr.*, 1963, 12:394-400.

Kindack et al, "Separation, identification and determination of lumichrome in swine feed and kidney", *Food Additives and Contaminants,* 1991, 8(6):737-748.

Klebanoff et al, "The risk of Childhood Cancer after Neonatal Exposure of Vitamin K", *New Eng. J. Med,* 1993, 329(13):905-908.

Kobayashi et al, "The molecular mechanism of mutation. Photodynamic action of flavins on the RNA-synthesizing system," *Chem. Abstracts,* 1983, 98(1), Abstract No. 1200.

Korycka-Dahl et al, "Photodegradation of DNA with Fluorescent Light in the Presence of Riboflavin, and Photoprotection by Flavin Triplet-State Quenchers", *Biochemica et Biophysica Acta,* 1980, 610:229-234.

Kovalsky et al., "Laser (Two-Quantum) Photolysis of Polynucleotides and Nucleoproteins: Quantitative Processing of Results", *Photochemistry and Photobiology,* 1990, 5(6):659-665.

Koziol, J., "Synthesis of Alloxazine Derivatives by Dealkylation of Isoalloxazines at N-10," *Bull. Pol. Acad. Sci.*, 1991, 39(1):37-39.

Kuratomi et al, "Studies on the Interactions Between DNA and Flavins", *Biochemica et Biophysica Acta,* 1977, 476:207-217.

Kurl et al, "A Metabolite of Riboflavin Binds to the 2,3,7,8-Tetrachlorodibenzo-*p*-dioxin (TCDD) Receptor", *Pharmacology,* 1985, 30:241-244.

Leontis et al, "The 5S rRNA loop E: Chemical probing and phylogenetic data versus crystal structure", 1998, *RNA* 4:1134-1153.

Lim et al, "Chemical probing of tDNAPhe with transition metal complexes: a structural comparison of RNA and DNA," 1993, *Biochemistry* 32:11029-11034.

Lytle et al,"Light Emitting Diode Source for Photodynamic Therapy", *SPIE*, vol. 1881, Optical Methods for Tumor Treatment and Detection, 1993, pp. 180-188.

Maddox, J., "The working of vitamin K," (1991) *Nature* 353(6346):695.

(56) References Cited

OTHER PUBLICATIONS

Malik et al, "New Trends in Photobiology—Bactericidal Effects of Photoactivated Porhyrins—an Alternative Approach to Antimicrobial Drugs," *J. Photochem. Photobiol* Pt.B: Biology, 1990, V:281-293.
Mallesh et al, "Synthesis and Biological Activities of Some New Substituted Alloxazines and Isoalloxazines: Part 1", *Acta Ciencia Indica,* 1989, XV(2):67-74.
Matthews et al., "Photodynamic therapy of viral contaminants with potential for blood banking applications," *Transfusion,* 1988, 28(1):81-83.
McCord et al, "Chemically induced dynamic nuclear polarization studies of yeast", 1984, *Biochemistry* 23:1935-1939.
McCormick, D.B., "Flavin Derivatives via Bromination of the 8-Methyl Substituent (1)", *J. Heter. Chem.*, 1970, 7:447-450.
Merenstein, et al, "Controversies concerning Vitamin K and the Newborn", Vitamin K Ad Hoc task Force, *Pediatrics,* 1993, 91(5):1001-1003.
Merrifield et al, Vitamin K as a fungistatic agent, 1965, *Appl. Microbio.* 13(5):660-662.
Merrifield et al, HY, "Factors affecting the antimicrobial acitivity of Vitamin K5", , *Appl. Microbio.*, 1965, 13(5):766-770.
Mitsuda et al, "Riboflavin—Indoles Interaction in Acid Solution", *J. Vitamin.*, 1970, 16:215-218.
Mohr et al, Agitation during Treatment Improves the Inactivation of Pathogens in Platelet Concentrates by UVB Irradiation, 2006, *Vox Sanguinis,* 91:suppl 3, P-371.
Moonen et al., "A photo-CIDNP study of the active sites of *Megasphaera elsdenii* and *Clostridium* MP flavodoxins," *FEBS Lett.*, 1982, 149(1):141-146.
Murata et al., "Effect of vitamins other than vitamin C on viruses: virus-inactivating activity of vitamin K5", *J. Nutr. Sci. Vitaminol.,* Tokyo, 1983, 29(6):721-724.
Murthy et al, "Chemical Modification of the N-10 Ribityl Side Chain of Flavins," *J. Biol. Chem.*, 1995, 270(48):28586-28594.
Naseem, et al., "Effect of alkylated and intercalated DNA on the generation of superoxide anion by riboflavin", *Bioscience Reports,* 1988, 8(5):485-492.
Nogami. et al, "Pharmacokinetic Aspects of Biliary Excretion. Dose Dependency of Riboflavin in Rat," *Chem. Pharm. Bull.*, 1970, 18:228-234.
North et al., "Photosensitizers as virucidal agents", *J. Photochem. Photobiol.* B: *Biol,* 1993, 17:99-108.
Ohkawa et al, "New Metabolites of Riboflavin Appeared in Rat Urine," *Biochem. Intl.*, Feb. 1983, 6(2):239-247.
Oka et al, "Urinary Lumichrome-Level Catabolites of Riboflavin are due to Microbial and Photochemical Events and Not Rat Tissue Enzymatic Cleavage of the Ribityl Chain", *J. Nutr.*, 1985, 115:496-499.
Ono et al, "Effects of Aging on the Formation of Ester Forms of Riboflavin in the Rat Lens," *Internat. J. Vit. Nutr. Res.*, 1986, 56:259-262.
Pamphilon et al, "Platelet concentrates irradiated with ultraviolet light retain satisfactory in vitro storage characteristics and in vivo survival", *British J. of Haematology,* 1990, 75, 240-244.
Parks et al,. "Photodegradation of Riboflavin to Lumichrome in Milk Exposed to Sunlight," *J. Dairy Sci.* 1977, 60(7):1038-1041.
Peak et al., "DNA Breakage Caused by 334-nm Ultraviolet Light is Enhanced by Naturally Occurring Nucleic Acid Components and Nucleotide Coenzymes", *Photochemistry and Photobiology,* 1984, 39(5):713-716.
Piette et al., "Alteration of Guanine Residues During Proflavine Mediated Photosensitization of DNA", *Photochemistry and Photobiology*,1981, 33:325-333.
Piette et al., "Production of Breaks in Single- and Double-Stranded Forms of Bacteriophage ☐X174 DNA by Proflavine and Light Treatment", *Photochemistry and Photobiology,* 1979, 30:369-378.
Pratt, et al, "Vitamin K5 as an Antimicrobial Medicament and Preservative", *J. Am. Pharm. Assn.*, 1950, 39(3):127-134.

Prodouz et al, "Use of Laser-UV for Inactivation of Virus in Blood Products", *Blood*, vol. 70, No. 2, Aug. 1987, pp. 589-592.
Radda et al, "Chemical and Photochemical Reductions of Flavin Nucleotides and Analogs," *Biochem.*, 1964, 3(3):384-393.
Rivlin, R.S., "Riboflavin Metabolism," *New Engl. J. Med.*, 1970, 283(9):463-472.
Roughead et al, "Qualitative and Quantitative Assessment of Flavins in Cow's Milk," *J Nutr.*, 1990, pp. 382-388.
Salim-Hanna et al, "Obtention of a Photo-Induced Adduct Between a Vitamin and an Essential Aminoacid. Binding of Riboflavin to Tryptophan", *Internat. J. Vit. Nutr. Res.*, 1987, 57:155-159.
Scheindlin et al, "The Action of Riboflavin on Folic Acid," *J. Am. Pharm. Assn.*, 1952, XLI:420-427.
Schoo et al, "Flavin-Containing Polyanions: Synthesis, Activity, and Immobilization in Polyelectrolye Complexes", *Macromolecules,* 1992, 25:1633-1638.
Shwartzman; G., "Antibacterial Properties of 4-Amino-2-Methyl-1-Naphthol Hydrocloride", *Proc. Soc. Exp. Biol. Med.*, 1948, 67:376-378.
Silva et al, "Light-Induced Binding of Riboflavin to Lysozyme", *Rad. Environm. Biophys.*, 1977, 14:303-310.
Silva et al., "Riboflavin-sensitized photoprocesses of tryptophan", *J. Photochem. Photobiol. B: Biol.*, 1994, 23:43-48.
Silva. et al, "A Light-Induced Tryptophan-Riboflavin Binding: Biological Implications", in *Nutritional and Toxicological Consequences of Food Processing,* Friedman, ed. Plenum Press, New York, 1991, pp. 33-48.
Simukova et al, "Conversion of Non-covalent Interactions in Nucleoproteins into Covalent Bonds: UV-Induced Formation of Polynucleotide-Protein Crosslinks in Bacteriophage Sd Virions", *FEVS Letters,* 1974, 38(3):299-303.
Smith et al, "The Photochemical Degradation of Riboflavin", *J. Am. Chem. Soc.*, 1963, 85:3285-3288.
Snyder et al, "Storage of platelet concentrates after high-dose ultraviolet B irradiation", *Transfusion*, vol. 31, No. 6, 1991, pp. 491-496.
Song et al, "Photochemical Degradation of Flavins—IV. Studies of the Anaerobic Photolysis of Riboflavin", *Photochem. Photobiol.,* 1967, 6:691-709.
Speck et al., "Further Observations on the Photooxidation of DNA in the Presence of Riboflavin", *Biochimica et Biphysica Acta,* 1976, 435:39-44.
Spranger, J. "Does vitamin K cause cancer?", *Eur. J. Pediatr.*, 1993, 152(2):174.
Steczko et al, "The Role of Tryptophan Residues and Hydrophobic Interaction in the Binding of Fiboflavin in Egg Yolk Flavoprotein", *Biochim. Biophys. Acta,* 1975, 393:253-266.
Swinehart et al, "Riboflavin-Tryptophan Complex Formation as a Criterion for "Buried" and "Exposed" Tryptophyl Residues in Proteins", *Biochem. Biophys. Acta,* 1965, 104:205-213.
Tapia et al, Photo-induced riboflavin binding to the tryptophan residues of bovine and human serum albumins *Radiat. Environ. Biophys.*, 1991, 30:131-138.
Toyosaki et al, "Structural analysis of the products of milk riboflavin photolysis", *Milchwissenschafi* , 1993, 48(11):607-609.
Treadwell et al, "Photochemical Degradation of Flavins. V. Chromatographic Studies of the Products of Photolysis of Riboflavin", *J. Chromatog.*, 1968, 35:376-388.
Treadwell et al, "Photoconversion of Riboflavin to Lumichrome in Plant Tissues," *Plant Physiol.*, 1972, 49:991-993.
Tsugita et al., "Photosensitized inactivation of ribonucleic acids in the presence of riboflavin", *Biochim. Biophys. Acta,* 1965, 103:360-363.
Tyrakowska et al. "A Fluorescence Study of Lumichrome Phototautomerism in Dodecylammonium Propionate Reversed Micelles", *J. Photochem. Photobiol. A.*, 1993, 72:235-241.
Uehara et al, "Effect of adenine on the riboflavin-sensitized photoreaction. II. Effect of adenine on the photodynamic inactivation of transforming deoxyribonucleic acid in the presence of riboflavin", , *J Biochemistry,* 1972, 71(5)805-810.
Uehara et al, "Effect of adenine on the riboflavin-sensitized photoreaction. I. Effect of adenine on the photodynamic inactivation of yeast alcohol dehydrogenase in the presence of riboflavin,"*J. Vitaminology,* 1971 17(3)148-154.

(56) References Cited

OTHER PUBLICATIONS

Van Schagen et al. "Photochemically Induced Dynamic Nuclear Polarization Study on Flavin Adenine Dinucleotide and Flavoproteins," *Biochemistry,* 1982,21(2):402-407.

Vest, M., "Vitamin K in medical practice; pediatrics", *Vitami. Horm.,* 1966, 24:649-663.

Webb et al, "Mutagenesis in *Escherichia coli* by Visible Light", *Science,* 1967, 156:1104-1105.

Woodcock et al., "Riboflavin Photochemical Degradation in Pasta Measured by High Performance Liquid Chromatography", *J. Food Sci.,* 1982, 47:545-549.

Yang et al, "Microbiological and Enzymatic Assays of Riboflavin Analogues", *J. Nutrition,* 1964, 64:167-172.

Zhizhina et al, "Formation of free radicals and DNA breaks after pulsed laser irradiation of DNA complexes with intercalating dyes", *Biofizika,* vol. 35, n 1, Jan.-Feb. 1990, pp. 47-52 (abstract only).

\* cited by examiner

REDUCTION OF CONTAMINANTS IN BLOOD AND BLOOD PRODUCTS USING PHOTOSENSITIZERS AND PEAK WAVELENGTHS OF LIGHT

This application claims priority to U.S. provisional application Ser. No. 60/822,726, filed Aug. 17, 2006. This application is also a continuation-in-part of Ser. No. 10/904,361, filed Nov. 5, 2004, now abandoned; which is a continuation of Ser. No. 10/357,599 filed Feb. 3, 2003 now U.S. Pat. No. 6,843,961; which is a continuation-in-part of Ser. No. 09/962,029 filed Sep. 25, 2001, now abandoned; which is a continuation-in-part of Ser. No. 09/596,429 filed Jun. 15, 2000 now U.S. Pat. No. 7,094,378.

BACKGROUND

Whole blood collected from volunteer donors for transfusion into recipients is typically separated into components such as red blood cells, white blood cells, platelets, plasma and plasma proteins, using apheresis or other known methods. Each of these separated blood components may be stored individually for later use and are used to treat a multiplicity of specific conditions and disease states. For example, the red blood cell component is used to treat anemia, the concentrated platelet component is used to control bleeding, and the plasma protein component is used frequently as a source of Clotting Factor VIII for the treatment of hemophilia.

In cell separation procedures, there are usually some small percentage of other types of cells which are carried over into a separated blood component. When contaminating cells are carried over into a separated component of cells in a high enough percentage to cause some undesired effect, the contaminating cells are considered to be undesirable. For example, white blood cells, are considered undesirable because they may transmit infections such as HIV and CMV may also cause other transfusion-related complications such as transfusion-associated Graft vs. Host Disease (TA-GVHD), alloimmunization and microchimerism.

Whole blood or blood products may also be contaminated with other undesirable pathogens such as viruses and bacteria. The term pathogen as used in this context includes undesirable contaminants such as donor white blood cells, parasites, bacteria and viruses.

Blood screening procedures may miss pathogenic contaminants, and sterilization procedures which do not damage cellular blood components but effectively inactivate all donor white blood cells, infectious viruses and other microorganisms have not heretofore been available.

The use of pathogen reducing agents, which include certain photosensitizers, or compounds which absorb light of defined wavelengths and transfer the absorbed energy to an energy acceptor, have been proposed for reduction of undesirable cells and microorganisms found in blood products or fluids containing blood products. Such photosensitizers may be added to the fluid containing blood or blood components and irradiated.

A number of systems and methods for irradiating pathogens in a fluid with light either with or without the addition of a photosensitizer are known in the art. For example, U.S. Pat. No. 5,762,867 is directed toward a system for activating a photoactive agent present in a body fluid with light emitting diodes (LEDs).

U.S. Pat. No. 5,527,704 is directed toward an apparatus containing LEDs used to activate a fluid containing methylene blue.

U.S. Pat. No. 5,868,695 discloses using LEDs having a red color and emitting light at a wavelength of 690 nm in combination with benzoporphyrin derivative photosensitizers to inactivate red blood cells. As taught in this patent, at a wavelength of 690 nm, red blood cells are essentially transparent to radiation, and as such, the benzoporphyrin derivatives absorb radiation at this wavelength to become activated. Also disclosed in this patent is the use of LEDs having a blue color and emitting light at a peak wavelength of 425 nm to inactivate platelets.

U.S. Pat. No. 5,658,722 discloses irradiating platelets using UVA1 light having an emission peak near 365 nm. This patent teaches that damage to platelets is caused by short UVA<345 nm, and unlike the present invention, calls for removing UVA wavelengths below 345 nm.

Use of UV light which is variably pulsed at a wavelength of 308 nm without the addition of a photosensitizer to inactivate virus in a washed platelet product is taught in an article by Prodouz et al., (Use of Laser-UV for Inactivation of Virus in Blood Products; Kristina Prodouz, Joseph Fratantoni, Elizabeth Boone and Robert Bonner; *Blood*, Vol 70, No. 2). This article does not teach or suggest the addition of a photosensitizer in combination with light to kill viruses.

One of the features associated with the use of UV light to irradiate red cells has been the propensity of this approach to induce methemoglobin (metHb) formation. In general, metHb levels in normal red cells is less than 1-2%. When levels exceed 10%, symptoms begin to appear in individuals suffering from methemoglobinemia. These include nausea, vomiting, difficulty breathing, discoloration of skin, etc. When levels reach 20-30% severe reactions, including death occurs.

UV light is known to be absorbed by hemoglobin in red cells, primarily through the porphyrin structure of the hemoglobin molecule. Once absorbed, it can result in a change in the oxidation state of the hemoglobin molecule from the $Fe^{2+}$ (ferrous) to $Fe^{3+}$ (ferric) state. This occurs via oxidation of the iron chelate. The $Fe^{3+}$ state is not capable of binding or transporting oxygen. This form of the molecule is known as methemoglobin. Normally, oxidation is reversible through several enzymatic systems in the red cell, which can reduce the $Fe^{3+}$ state back to $Fe^{2+}$. Several chemical agents are also known to be able to affect this reduction chemistry. These include methylene blue and riboflavin.

One study on the ability of riboflavin to cause a reduction in hemoglobin from the metHb form back to the normal hemoglobin form was discussed in Dotsch et al. "Comparison of Methylene Blue, Riboflavin, and N-acetylcysteine for the Reduction of Nitric Oxide-induced Methemoglobinemia" (*Crit. Care Med* 2000, Vol. 28, No. 4, pp. 958-961). The reference showed a concentration effect for this chemistry, with optimal levels being observed at 120 µM.

At the time this study was done, using concentrations of riboflavin greater than 120 µM was not possible due to the solubility limits of riboflavin.

The present invention is directed toward the reduction of pathogens which may be present in red blood cells using Uv light in combination with an endogenous photosensitizer, without extensive formation of methemoglobin or excessive hemolysis of the red blood cells upon illumination with UV light.

SUMMARY

This invention is directed to a method for reducing pathogens which may be contained in red blood cells and includes the steps of adding an isoalloxazine photosensitizer to the red blood cells to form a mixture, and exposing the mixture of the red blood cells and the photosensitizer to light having a peak wavelength of approximately 302 nm.

The method of this invention also reduces the formation of methemoglobin and hemolysis of the red blood cells.

This invention is also directed toward a treatment chamber for reducing pathogens in a fluid containing red blood cells and a photosensitizer which includes at least one radiation emitting source emitting radiation at a peak wavelength of approximately 302 nm, a support platform for holding the fluid containing red blood cells and photosensitizer to be irradiated; and a control unit for controlling the radiation emitting source.

DETAILED DESCRIPTION

Photosensitizers useful in this invention include endogenous photosensitizers. The term "endogenous" means naturally found in a human or mammalian body, either as a result of synthesis by the body or because of ingestion as an essential foodstuff (e.g. vitamins) or formation of metabolites and/or byproducts in vivo. When endogenous photosensitizers are used, particularly when such photosensitizers are not inherently toxic or do not yield toxic photoproducts after photoradiation, no removal or purification step is required after decontamination, and the decontaminated product can be directly administered to a recipient in need of its therapeutic effect.

Examples of such endogenous photosensitizers which may be used in this invention are alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazineadenine dinucleotide (flavin adenine dinucleotide [FAD]) and alloxazine mononucleotide (also known as flavin mononucleotide [FMN] and riboflavine-5-phosphate). The term "alloxazine" includes isoalloxazines.

One mechanism by which these photosensitizers may inactivate pathogens is by interfering with nucleic acids, so as to prevent replication of the nucleic acid. As used herein, the term "reduction of a pathogen" means totally or partially preventing the pathogen from replicating, either by killing the pathogen or otherwise interfering with its ability to reproduce. Specificity of action of the preferred photosensitizer is conferred by the close proximity of the photosensitizer to the nucleic acid of the pathogen and this may result from binding of the photosensitizer to the nucleic acid. "Nucleic acid" includes ribonucleic acid (RNA) and deoxyribonucleic acid (DNA).

Upon exposure of the photosensitizer to light, the photosensitizer will absorb the light energy, causing photolysis of the photosensitizer and any nucleic acid bound to the photosensitizer. In this invention, the photosensitizer used in the examples is 7,8-dimethyl-10-ribityl isoalloxazine (riboflavin).

Besides undesirable donor white blood cells, other pathogens which may be reduced using pathogen reduction agents or photosensitizers include, but are not limited to, viruses (both extracellular and intracellular), bacteria, bacteriophages, fungi, blood-transmitted parasites, and protozoa. Exemplary viruses include acquired immunodeficiency (HIV) virus, hepatitis A, B and C viruses, sinbis virus, cytomegalovirus, vesicular stomatitis virus, herpes simplex viruses, human T-lymphotropic retroviruses, lymphadenopathy virus LAV/IDAV, parvovirus, transfusion-transmitted (TT) virus, Epstein-Barr virus, BVDV, HAV, and others known to the art. Bacteriophages include Φ X174, Φ 6, λ, R17, $T_4$, and $T_2$. Exemplary bacteria include but are not limited to *P. aeruginosa, S. aureus, S. epidermis, L. monocytogenes, E. coli, K pneumonia, Y. enterocolitica* and *S. marcescens*.

The photosensitizer may be added directly to the fluid to be pathogen reduced, or may be flowed into the photopermeable container separately from the fluid being treated, or may be added to the fluid prior to placing the fluid in the photopermeable treatment container. The photosensitizer may also be added to the photopermeable container either before or after sterilization of the treatment container.

The fluid containing the photosensitizer may also be flowed into and through a photopermeable container for irradiation, using a flow through type system. Alternatively, the fluid to be treated may be placed in a photopermeable container which is agitated and exposed to photoradiation for a time sufficient to substantially reduce the pathogens, in a batch-wise type system.

After treatment, the blood or blood product may be stored for later delivery to a patient, concentrated, infused directly into a patient or otherwise processed for its ultimate use.

Figure 1:
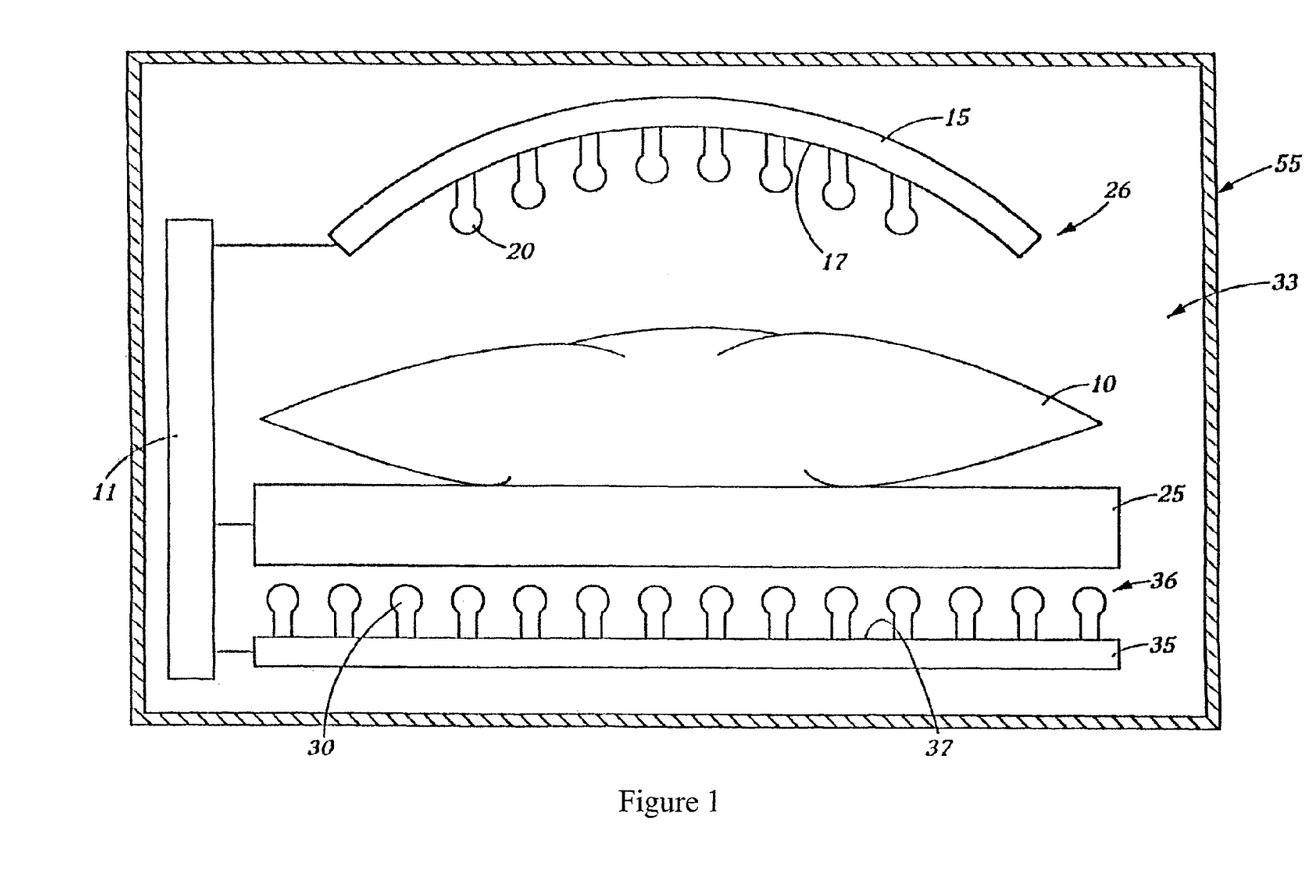
FIG. 1 is a cross-sectional view of a treatment chamber which may be used in the present invention.

FIG. 1 shows, in a cross-sectional view, the inside of a radiation or treatment chamber of one type of apparatus that may be used in the present invention. The treatment chamber shown in FIG. 1 may be used in batch-wise systems; however, it should be noted that similar elements may also be used in flow-through systems. It should be noted that throughout the description of the invention, like elements have been given like numerals. The apparatus 55, used for inactivating a fluid which may contain pathogens, consists of an internal chamber 33 having at least one source of radiation 26. In one preferred embodiment, the internal chamber may contain a second source of radiation 36. Each radiation source 26 and 36 respectively, is depicted as including a plurality of discrete radiation-emitting elements. The internal chamber 33 further consists of a support platform, shelf or platen 25 for supporting the fluid container 10 containing the fluid to be irradiated, and a control unit 11.

As introduced above, two sources of radiation are shown within internal chamber 33. Radiation source 26 may be located along the top portion of the internal chamber 33 above the container 10 which holds or contains the fluid to be irradiated, while radiation source 36 may be located along the bottom portion of the internal chamber 33 below the container 10. Although not shown, radiation sources may also be located along some or all of the sides of the internal chamber 33 perpendicular to the container 10. The radiation or treatment chamber 55 may alternatively contain a single radiation source at any location within the internal chamber 33 and still comply with the spirit and scope of the present invention.

The radiation source including a plurality of radiation-emitting elements collectively designated as source 26 includes an upper support substrate 15 containing a plurality of discrete radiation emitting elements or discrete light sources (see discrete source 20 as one example) mounted thereon. The support substrate 15 may be in an arcuate shape as shown, in a flat shape, or in other configurations which are not shown but are known in the art. Thus, the upper support substrate 15 could also be in a shape other than arcuate without departing from the spirit and scope of the invention.

As further depicted in FIG. 1, the radiation source collectively designated as discrete source 36 includes a lower support substrate 35 which also contains a plurality of discrete radiation emitting elements or discrete light sources (see discrete source 30 as another example). Lower support substrate 35 preferably runs parallel to support platform 25. The lower support substrate 35 may be substantially flat as shown, or may be in an arcuate shape similar to element 15 above, or may be in a shape other than arcuate, without departing from the spirit and scope of the invention.

Figure 2:
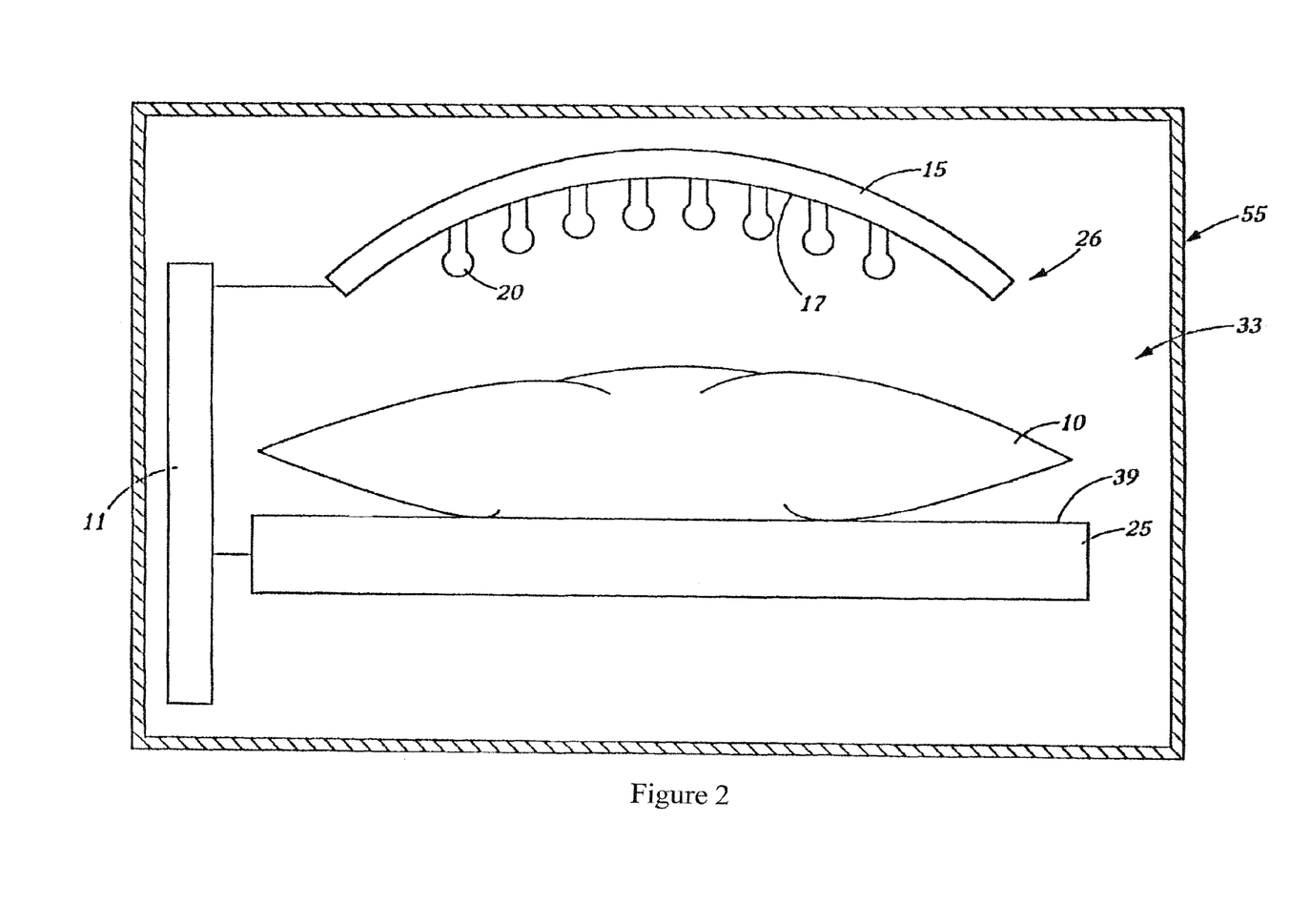
FIG. 2 is a cross-sectional view of a treatment chamber like that of FIG. 1, but with an alternative reflective surface that may also be used in the present invention.

As shown in FIG. 1, the support substrates 15 and 35 may include at least one reflective surface, and as shown, may include two or more reflective surfaces 17 and 37 thereon. Reflective surface 17 is shown as running contiguous with upper support substrate 15. Reflective surface 37 is shown as running contiguous with lower support substrate 35. The reflective surfaces 17 and 37 may also run contiguously with only a portion of support substrates 15 and 35. As shown in FIG. 1, discrete light source devices 20 and 30 extend outwardly away from the surface of the support substrates 15 and 35. Alternatively, a discrete light source could be recessed into the surface such that the surface surrounds each discrete light source in a parabolic shape (not shown). The support substrate may or may not have reflective surfaces. In a further alternative configuration, the reflective surface may not contain any light sources. Such a reflective surface containing no light sources (not shown) may be located within the treatment chamber on a side opposite from the radiation source. As shown in FIG. 2, the support platform 25 may have a reflective surface 39. This reflective surface 39 on support platform 25 may be in place of, or may be in addition to, another reflective surface (see element 17 as one example) within the treatment chamber. There may also be no reflective surfaces at all within the treatment chamber.

In any of these reflective surface embodiments, the reflective surface may be coated with a highly reflective material which serves to reflect the radiation emitted from the lights back and forth throughout the treatment chamber until the radiation is preferably completely absorbed by the fluid being irradiated. The highly reflective nature of the reflective surface reflects the emitted light back at the fluid-filled bag or container 10 with minimum reduction in the light intensity.

In FIG. 1, support platform 25 is positioned within the internal treatment chamber 33. The support platform 25 may be located substantially in the center of the radiation or treatment chamber (as shown in FIG. 1), or may be located closer to either the top portion or the bottom portion of the treatment chamber without departing from the spirit and scope of the present invention. The support platform 25 supports the container 10 containing the fluid to be irradiated. The support platform 25 may also be defined as a platen or a shelf. Additionally or alternatively, the platform 25 may be made of a photopermeable material to enable radiation emitted by the lights to be transmitted through the platform and penetrate the fluid contained within the container 10. The platform may also be a wire or other similar mesh-like material to allow maximum light transmissivity therethrough.

The support platform 25 is preferably capable of movement in multiple directions within the treatment chamber. One type of agitator, such as a Helmer flatbed agitation system available from Helmer Corp. (Noblesville, Ind., USA) may be used. This type of agitator provides to and fro motion. Other types of agitators may also be used to provide a range of motion to the fluid contained within the container 10, without departing from the spirit and scope of the invention. For example, the support platform might be oriented in a vertical direction and the light sources may be rotated about a horizontal axis. The support platform 25 may alternatively rotate in multiple possible directions within the radiation chamber in varying degrees from between 0° to 360°. Support platform 25 may also oscillate back and forth, or side to side along the same plane. As a further alternative, one or more of the light sources may also move in a coordinated manner with the movement of the support platform. Such oscillation or rotation would enable the majority of the photosensitizer and fluid contained within the container 10 to be exposed to the light emitted from each of the discrete radiation sources (e.g. discrete sources 20 and 30), by continually replacing the exposed fluid at the light-fluid interface with fluid from other parts of the bag not yet exposed to the light. Such mixing continually brings to the surface new fluid to be exposed to light.

The movement of both the support platform 25 and/or the radiation sources 26 and 36 may be controlled by control unit 11. The control unit 11 may also control the rate of light emission.

In a preferred embodiment each discrete light source 20 and 30 emits a peak wavelength of light to irradiate the fluid contained in bag 10. The peak wavelength of light emitted by each discrete light source is selected to provide irradiation of a sufficient intensity to activate both the photosensitizer in a pathogen inactivation process as well as to provide sufficient penetration of light into the particular fluid being irradiated, without causing significant damage to the blood or blood components being irradiated. The preferred photosensitizer is riboflavin. To irradiate a fluid containing red blood cells and riboflavin, it is desirable that each discrete light source 20 and 30 be selected to emit light at a peak wavelength of between 302-306 nm.

Figure 4:
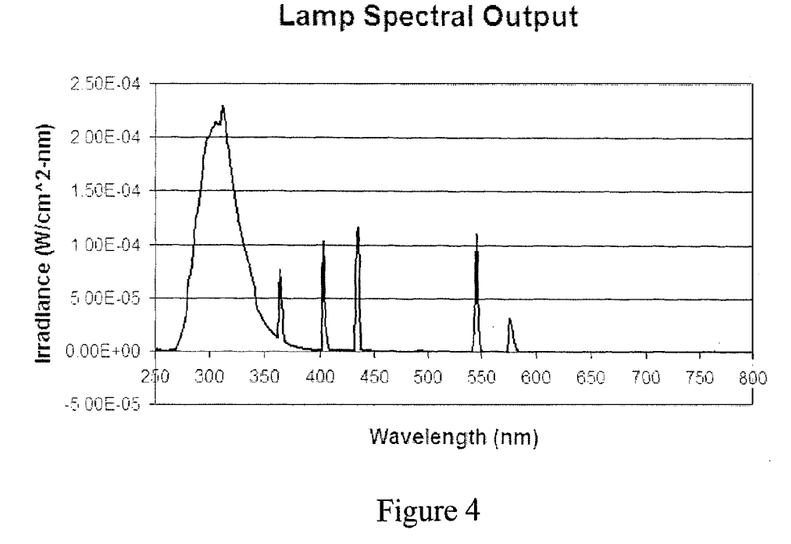
FIG. 4 is a graph depicting the light spectrum of one type of bulb which may be used in the present invention.

FIG. 4 is a graph showing the spectral output of lamps which may be used in this invention. As can be seen, the bulbs emit light energy in a range of approximately 270-400 nm, with a phosphor peak intensity occurring at a wavelength of between 302-306 nm.

The term peak wavelength as defined herein means that the light is emitted in a narrow range centered around a wavelength having a particular peak intensity. In an embodiment, the light may be centered around a narrow range of UV light at an approximate wavelength of 302 nm. The term "approximate" means the light may be ±5 nm around 302 nm. The term light source or radiation source as defined herein means an emitter of radiant energy, and includes energy in the ultraviolet range, as further described below.

Figure 3:
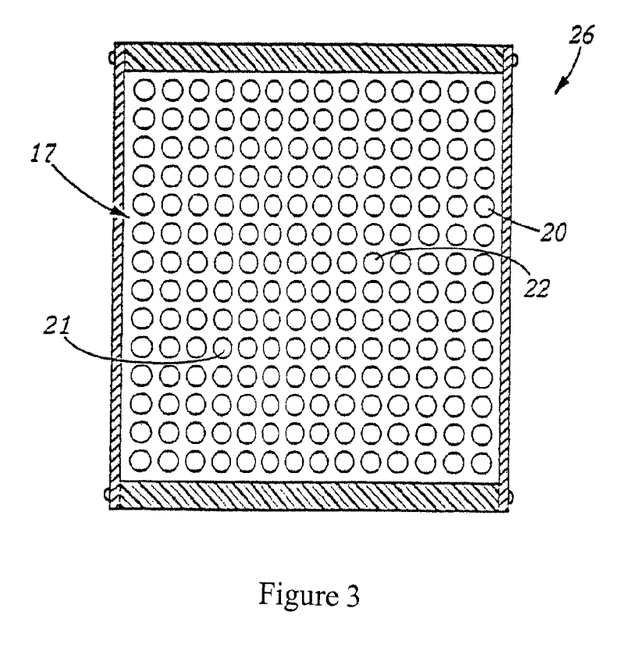
FIG. 3 is a plan view of an array of LEDs that may be used in the present invention.

As shown in FIG. 3, each radiation source 26 may consist of a bank or array of a plurality of discrete LEDs devices. LED devices 20, 21 and 22 are self-contained emitters of radiation. Each LED emits a single color of light when an electrical current is applied. Each of the LED devices in the array 26 may also emit light in the same peak wavelength, which for red blood cells is preferably selected to be around approximately 302 nm.

Figure 5:
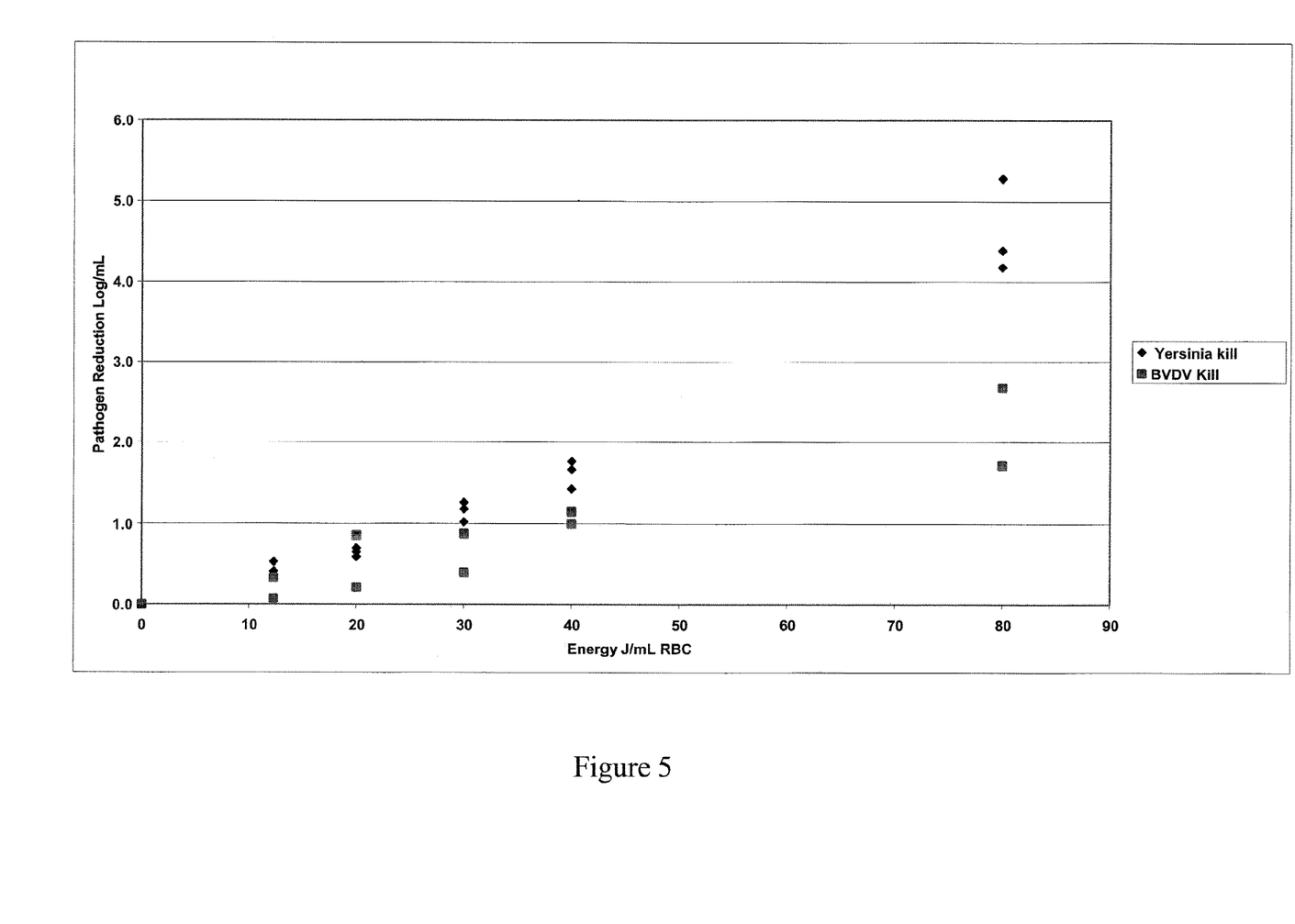
FIG. 5 is a graph of log pathogen reduction as a function of energy dose.

The discrete radiation sources or lights may be arranged in banks or arrays containing multiple rows of individual lights, or may be arranged in a single row (not shown). As shown in FIG. 5, if LED devices are used, a plurality of discrete LED devices may be arranged in multiple rows. The lights may also be staggered or offset from each other (not shown). If a bank or an array of LED lights is located in both the top and the bottom of the irradiation chamber 55 (see FIG. 1), or in a vertical orientation as described above, each bag or container 10 containing fluid to be irradiated will be exposed to light on both the top and the bottom surfaces (or on both sides of the bag if in a vertical orientation). A reflective surface 17 (like that shown in FIG. 1) may also be part of the array.

One or more light sources may be used in the irradiation apparatus, depending on the output required to substantially reduce pathogens which may be present in the blood product, and without substantially damaging the blood component being irradiated.

As described above, the lights used in this invention may be LED devices or other narrow bandwidth sources such as fluorescent light sources. The Ushio GT25T8E UV-B lamp is one such fluorescent source which may be used which has 10th percentile bandwidth points at approximately 278 nm and 353 nm. The peak phosphor power is at 306 nm. The UV-B region of the spectrum is 290 nm to 320 nm.

Emitting light in a narrow spectrum may be beneficial to the blood product being irradiated because all non-useful wavelengths of light which might damage the blood or blood component being irradiated are reduced or eliminated.

EXAMPLE 1

To determine the effect UV light and riboflavin have on the pathogen reduction of red blood cells, whole blood units were leukoreduced with a leukoreduction filter and centrifuged to initially separate the plasma component from the cellular component. The plasma component was removed and saline was added to wash the cellular component. The washed red blood cell component was diluted with 500 μM riboflavin in 0.9% saline to a hematocrit of 30%. The red blood cells were illuminated with UV light in a range of energies, from 5.6 J/cm$^2$ (19 J/mL RBCs) to 16.6 J/cm$^2$ (40 J/mL RBCs), with bulbs having a peak wavelength of approximately 302 nm. After treatment, the cells were centrifuged to express the riboflavin solution and the commercially available storage solution AS3 was added. The pathogen reduced cells were stored at 4° C. These cells are referred to as treated red blood cells.

As shown in FIG. 5, at 40 J/mL RBCs, bovine viral diarrhea virus (BVDV, an enveloped virus and model for human Hepatitis C) was reduced in red blood cells by 1.1 logs. *Yersinia enterocolitica* (a bacterium) was reduced by 1.6 logs.

Figure 6:
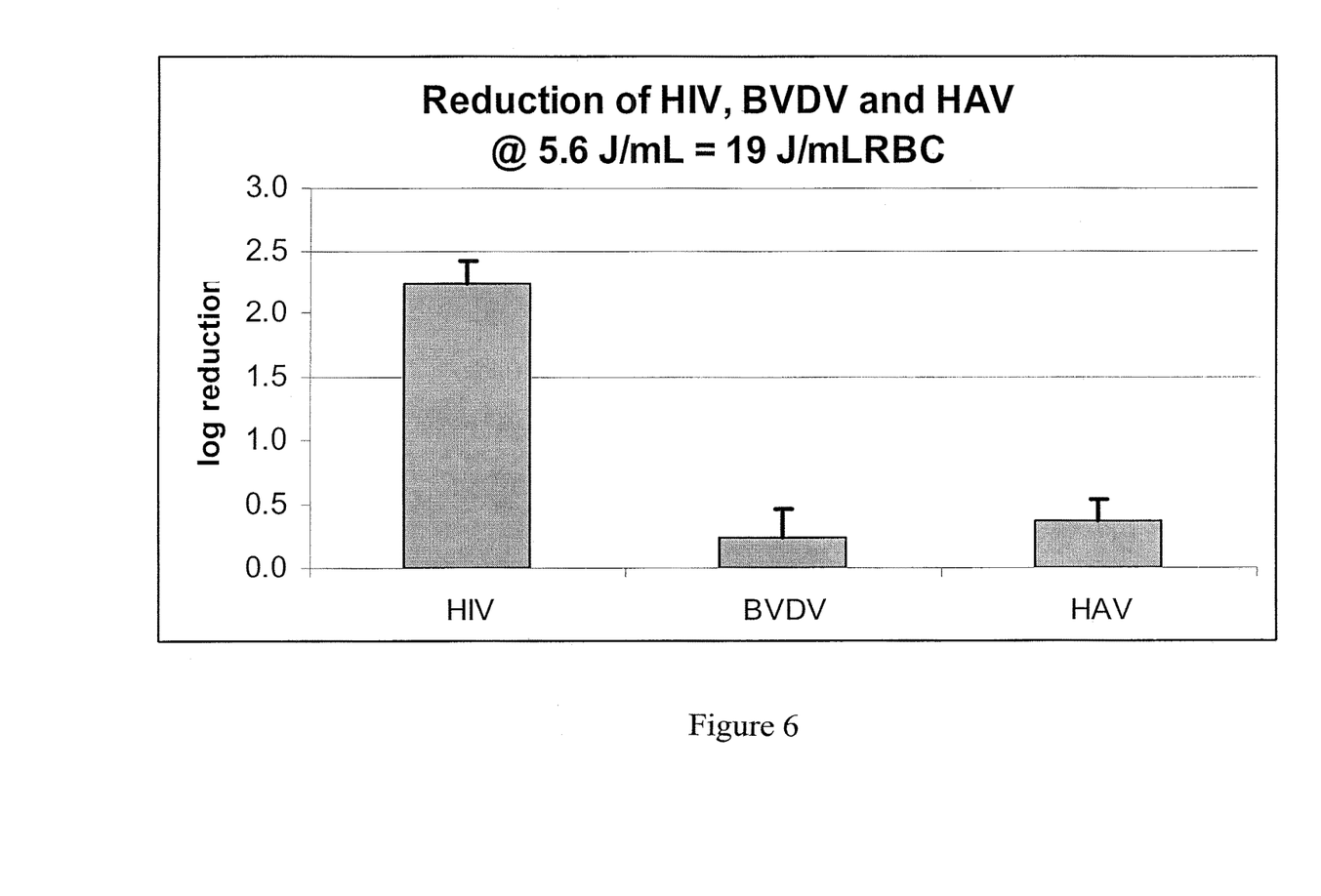
FIG. 6 is a graph of log pathogen reduction at 19 J/mL red blood cells.

As shown in FIG. 6, at half the energy (19 J/mL RBCs), the HIV virus is reduced by 2.25 logs, while BVDV and hepatitis A virus (HAV, a non-enveloped virus that infects humans) were reduced by 0.5 logs. This is an expected result, since half the energy was used as compared to FIG. 5 above.

FIGS. 5 and 6 show that approximately 302 nm of light with riboflavin is capable of reducing pathogens in red blood cells.

EXAMPLE 2

In addition to preventing replication of pathogens which may be present in red blood cells, the addition of riboflavin appears to prevent oxidation of hemoglobin to the methemoglobin (metHb) form as well as to decrease red cell hemolysis due to the exposure to UV light.

Studies which compare both metHb formation and hemolysis in samples with varying doses of riboflavin (0, 50, 500 Micromolar) were conducted to determine if there is a concentration dependence and if this effect can be correlated with the presence of riboflavin. Since riboflavin's absorbance of light in this region is minimal (unless bound to DNA or RNA), it is not expected that these results are due to simple screening or shielding of the hemoglobin from UV light.

Figure 7:
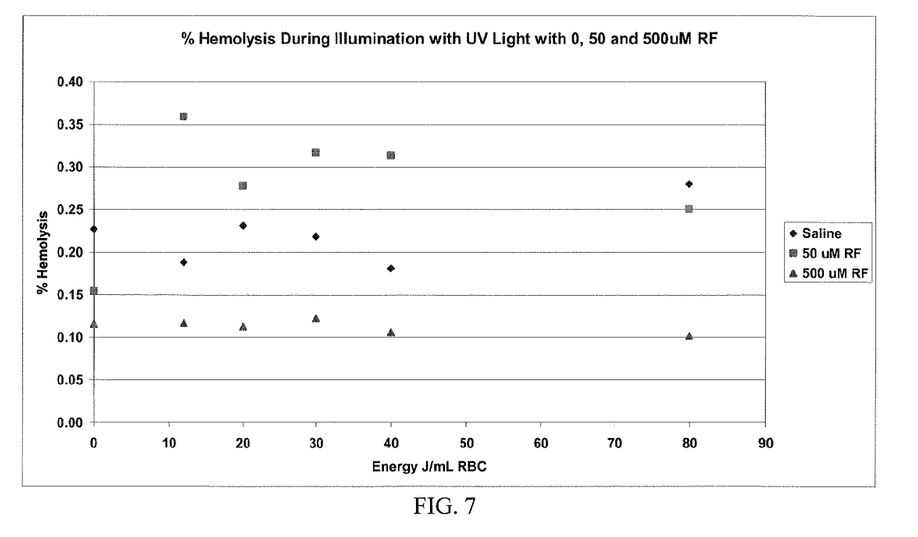
FIG. 7 is a graph comparing the percentage hemolysis of red blood cells as a function of energy dose.

FIG. 7 shows the % hemolysis of treated red blood cells at varying energy levels (from 0-40 J/mL red blood cells and 80 J/mL red blood cells having a peak wavelength of approximately 302 nm) for each unit illuminated in saline, 50 μM (shown in legend as 50 uM RF) and 500 μM (500 uM RF) riboflavin. One replicate was illuminated for each riboflavin concentration tested. Hemolysis values were consistently lower for the red blood cells containing 500 μM riboflavin, with the next highest values observed for the red blood cells containing saline and then 50 μM riboflavin. The lower hemolysis values observed in the 500 μM riboflavin samples may indicate that higher concentrations of riboflavin protect the red cells from damage by UV light. There may be a threshold in riboflavin concentration at which UV light can no longer easily affect the RBCs. Any exposure below this threshold would potentially damage the RBCs. This may explain why the 50 μM samples and the saline samples are similar, with the 50 μM samples higher than the saline samples for most of the energies assessed.

Figure 8:
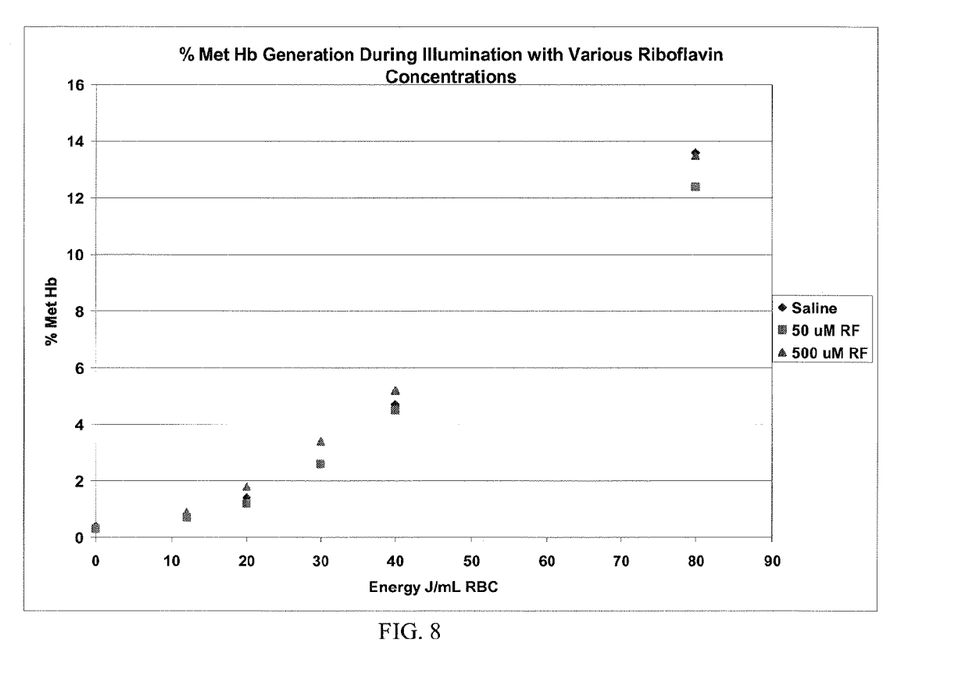
FIG. 8 is a graph comparing the percentage methemoglobin generated during illumination as a function of energy dose.

FIG. 8 shows the % metHb generation during illumination of treated red blood cells at varying energy levels (from 0-40 J/mL red blood cells and 80 J/mL red blood cells) for each unit illuminated in saline, 50 μM (shown in legend as 50 uM RF) and 500 μM (500 uM RF) riboflavin. One replicate was illuminated for each riboflavin concentration tested. FIG. 8 shows that methemoglobin measurements were essentially the same for each riboflavin concentration tested at each energy level.

Crossmatch scores were measured for all illumination samples using autologous plasma and Ortho-Clinical gel cards (not shown). All IgG scores were zero—indicating no binding of protein to the red blood cells and therefore no detectable damage.

Figure 9:
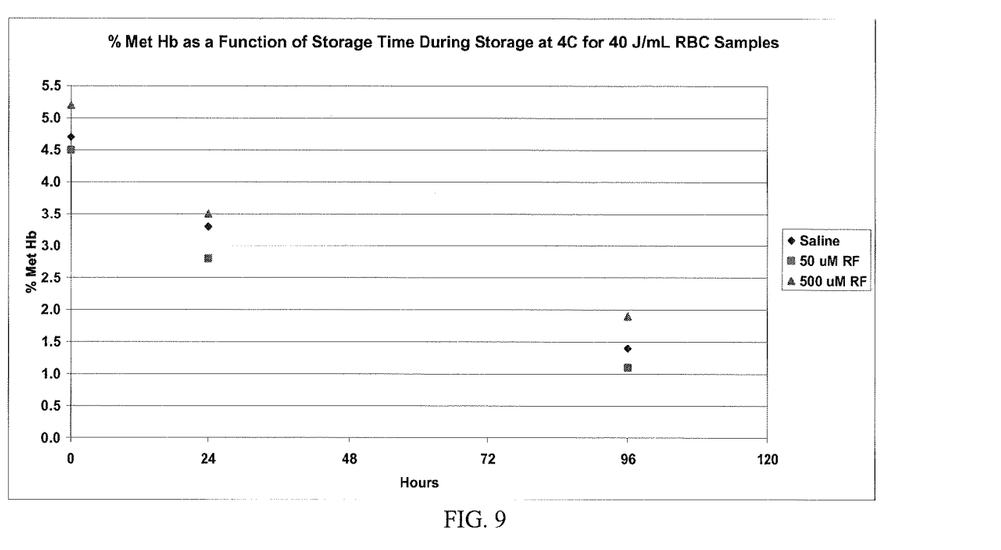
FIG. 9 is a graph comparing the percentage of methemoglobin as a function of storage time.

As shown in FIG. 9, the percentage of methemoglobin decreases over time during storage. Methemoglobin values decrease to acceptable levels (<3%) by Day 4 (96 hours) for all samples at the various riboflavin concentrations tested.

It is believed that the reason for the successful treatment of red cells using UV light in the wavelength range of approximately 270-400 nm and having an approximate peak wavelength of 302 nm is due to a reduction in the absorbance of light by the hemoglobin molecule in this region. Another potential reason for this unique and unexpected observation and outcome is that the presence of riboflavin at a concentration of 500 μM is able to protect the hemoglobin in the cells from oxidation due to UV light chemistry via the chemical reducing capacity of the riboflavin.

Any type of bulbs, either fluorescent or LEDs which emit light in a wavelength range between 270-400 nm may be used. Filters which filter out undesired wavelengths of light except light in the range of approximately 302 nm may also be used to obtain an approximate peak wavelength.

If desired, the light sources 20 and 30 may be pulsed. Pulsing the light may be advantageous because the intensity of light produced by the light sources may be increased dramatically if the lights are allowed to be turned off and rested between light pulses. Pulsing the light at a high intensity also allows for greater depth of light penetration into the fluid being irradiated, thus allowing a thicker layer of fluid to be irradiated with each light pulse.

Figure 10:
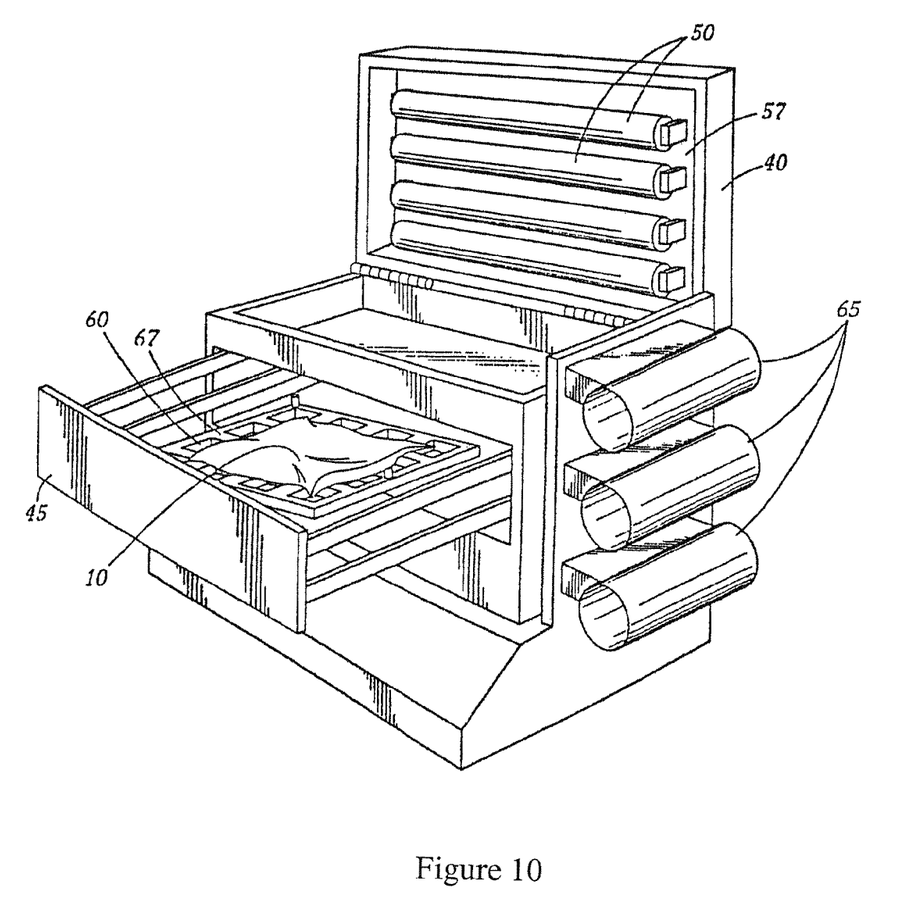
FIG. 10 is another embodiment of a treatment chamber which may be used in the present invention.

FIG. 10 shows an alternative embodiment of an irradiation or treatment chamber to be used with the present invention. A bank of light sources 50 which emit peak wavelengths of light and which may or may not be capable of being pulsed, may be located within the top of the irradiation chamber extending from lid 40. Although not shown in FIG. 10, a bank of lights may also be located in the bottom of the irradiation chamber as well. A reflective surface 57 is shown as part of the inner surface of lid 40; however, reflective surface 57 or another one or more surfaces (not shown) may be located anywhere within the radiation chamber as introduced above.

The lid 40 is capable of being opened and closed. During exposure of the bag 10 containing the fluid to be irradiated to the light sources, the lid 40 is in a closed position (not shown). To add or remove the bag 10 containing the fluid to be irradiated from the irradiation chamber, a drawer 45 located on the front of the irradiation chamber may be disposed in an open position (as shown). During the irradiation procedure, the drawer 45 is placed in a closed position (not shown).

The light sources 50, as shown in FIG. 10, may be fluorescent or incandescent tubes, which stretch the length of the irradiation chamber, or may be a single light source which extends the length and width of the entire chamber (not shown). The LEDs shown in FIG. 3 may also be used in this embodiment.

As shown in FIG. 10, the support platform or platen 67 may be located within and/or forming part of drawer 45. The support platform 67 may contain gaps 60 or holes or spaces within the platform 67 to allow radiation to penetrate through the gaps directly into the container 10 containing fluid to be irradiated.

A cooling system may also optionally be included. As shown in FIG. 10, air cooling using at least one fan 65 may be preferred but it is understood that other well-known systems can also be used. Although not shown in FIG. 10, the method may also include the use of temperature sensors and other cooling mechanisms where necessary to keep the temperature below temperatures at which desired proteins and blood components in the fluid being irradiated are damaged. Preferably, the temperature is kept between about 0° C. and about 45° C., more preferably between about 4° C. and about 37° C., and most preferably about 28° C.

Although described primarily with reference to a stand alone irradiation device used to irradiate individual bags (batch process), peak wavelengths of light may be used to irradiate blood or blood components in a flow-through irradiation system as well, without departing from the scope of the present invention.

What is claimed is:

1. A method for reducing pathogens in a fluid containing red blood cells comprising:
reducing pathogens in the fluid while reducing the formation of methemoglobin in the fluid containing red blood cells and reducing hemolysis of the red blood cells by:
adding riboflavin to the fluid at a concentration of 500 µM; and
exposing the mixture of the fluid and the riboflavin to light with a wavelength of 302 nm, wherein all light except light with the wavelength of 302 nm is filtered out wherein an exposed fluid is obtained.

2. The method of claim 1 wherein the exposing step comprises exposing the mixture to pulsed light at the wavelength of 302 nm.

3. The method of claim 1 wherein the method reduces the formation of methemoglobin in the exposed fluid to less than 3%.

4. The method of claim 1 further comprising a step of storing the exposed fluid.

5. The method of claim 4 wherein the method reduces the formation of methemoglobin during storage of the exposed fluid.

6. The method of claim 1 further comprising:
mixing the fluid and riboflavin during the exposing step to expose the majority of the fluid to the light.

* * * * *